United States Patent [19]

Decker et al.

[11] 4,339,236

[45] Jul. 13, 1982

[54] LOW FOAM SCOURING AGENTS

[75] Inventors: Quintin W. Decker, St. Albans; Erich Marcus, Charleston; Harry T. Zika, S. Charleston, all of W. Va.

[73] Assignee: Union Carbide Corporation, Danbury, Conn.

[21] Appl. No.: 179,970

[22] Filed: Aug. 21, 1980

Related U.S. Application Data

[63] Continuation-in-part of Ser. No. 879,252, Feb. 21, 1978, abandoned.

[51] Int. Cl.$^3$ .......................... B08B 3/00; C07C 69/36
[52] U.S. Cl. ........................................ 8/137; 252/170; 560/198; 8/139
[58] Field of Search ..................... 560/198; 252/170; 8/137, 139

[56] References Cited

U.S. PATENT DOCUMENTS

| | | | |
|---|---|---|---|
| 2,480,185 | 8/1949 | Fife et al. | 560/198 |
| 2,570,037 | 10/1951 | Smith et al. | 560/198 |
| 3,549,543 | 12/1970 | Klestshler et al. | 560/198 |
| 3,773,668 | 11/1973 | Denis et al. | 252/152 |
| 4,115,415 | 9/1978 | Yoshihara et al. | 560/198 |

FOREIGN PATENT DOCUMENTS

| | | |
|---|---|---|
| 234389 | 2/1960 | Australia . |
| 860691 | 11/1978 | Belgium . |
| 1465700 | 2/1977 | United Kingdom . |

*Primary Examiner*—Natalie Trousof
*Assistant Examiner*—Vera C. Clarke
*Attorney, Agent, or Firm*—Henry H. Gibson

[57] ABSTRACT

Esters of lower aliphatic dibasic acids and fatty alcohol alkoxylates have been prepared having excellent low-foaming and scouring properties.

10 Claims, No Drawings

LOW FOAM SCOURING AGENTS

This application is a continuation-in-part of application Ser. No. 879,252, filed Feb. 21, 1978, now abandoned.

BACKGROUND OF THE INVENTION

This invention pertains to esters of lower aliphatic dibasic acids and fatty alcohol alkoxylates and more particularly to esters made from fatty alcohol alkoxylates or fatty alcohol adducts of alkylene oxides having 2 to 3 carbon atoms.

The increasing costs of energy have intensified the need for energy conservation in all phases of life. This is particularly true in the textile industry where large amounts of energy are needed in the heating of water used in the wet processing of fabric and yarn. The need for a cotton or polyester-cotton low-foaming surfactant having good low-temperature scouring properties is one of the needs which has arisen during the energy crisis.

One of the requirements for a low-foam surfactant is a significant measure of insolubility in the substrate liquid. With most nonionic surfactants, this is generally manifested in a low cloud point. Another requirement for a low-foam surfactant is that it must be a good surface tension depressant. The surfactant or surface active agent will concentrate at the surface of the liquid where foam will be degraded. At this point the surfactant must have the ability to lower the surface tension of the bubble wall to a point lower than that of the aqueous solution, resulting in rapid drainage of liquid from the bubble. The third requirement of low-foam surfactants, imposed by ecological restrictions, is ready biodegradability.

A class of nonionic surfactants used in the past have been prepared by alkoxylation of fatty alcohols to afford alkoxylates. It is also known that non-ionic surfactants can be prepared by the esterification of fatty alcohol alkoxylates. For example, Japanese patent application No. 46-17476 discloses the product obtained by reacting 10 moles of ethylene oxide with a $C_{18}$ fatty alcohol followed by the reaction of the resultant ethoxylate with adipic acid. The use projected for this was as a lubricant for preventing polyester filaments agglutination. Its use as a low-foam scouring agent was not taught.

U.S. Pat. No. 3,382,285 discloses the composition obtained by the random addition of ethylene oxide and propylene oxide to a mixture of $C_{12}$ to $C_{20}$ fatty alcohols. These products are described as low-foam biodegradable surfactants.

U.S. Pat. No. 3,956,401 describes the preparation of low-foam biodegradable surfactants by reacting alkylene oxides with $C_7$ to $C_{10}$ alcohols.

Further, the reaction of dodecanol, succinic anhydride and polyethylene glycol (molecular weight 4,000) to yield nonionic surfactants was disclosed in Israel Pat. No. 38,521 (Chemical Abstracts, Volume 83, 117615, 1975). Here one carboxyl group was linked to the dodecanol and the other capped with an ethylene oxide adduct. No information is given as to the foaming properties of the resultant product.

There is also disclosed in U.S. Pat. No. 3,549,543 low foaming, washing, and cleansing compositions consisting essentially of a mixture of 3 types of polyoxyalkylene compounds, one of which compounds can be a fatty alcohol alkoxylate ester.

It is an object of this invention to provide low-temperature, low-foam scouring agents.

In accordance with the present invention there has been discovered a method of cleaning cotton or polyester-cotton articles under conditions of low temperature and low-foam which comprises contacting said cotton or polyester-cotton articles with a liquid cleansing agent comprising an aqueous solution of a nonionic scouring agent having the formula:

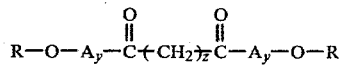

wherein R is alkyl having from 11 to 18 carbon atoms or alkyl substituted phenyl wherein the alkyl contains about 7 to about 12 carbon atoms, A is a divalent radical selected from the group consisting of oxyethylene units and mixtures of oxyethylene units with oxypropylene units up to a ratio of about 1:1; z is an integer having values of 0 or 1 and y is an integer having values of 5 to about 12.

The mixed oxyalkylene units can be either a block or random ethoxy/propoxy combination obtained by using a mixture of ethylene oxide and propylene oxide in a condensation reaction with a fatty alcohol having 11 to 18 carbon atoms. A random combination of these oxyalkylene units is preferred. Blocks of ethoxy or propoxy units achieved by using alternate interaction of a fatty alcohol with the corresponding alkylene oxide afford scouring agents in the practice of this invention which have greater foaming tendencies, a property to be eschewed. The scouring agent of this invention is obtained by esterification of oxalic or malonic acid with fatty alcohol alkylene oxide adducts.

When scouring agents containing mixed oxyalkylene units are used, it is preferred to use a large excess of oxyethylene to oxypropylene units. While up to 1 part of oxypropylene units per unit of oxyethylene can be used, one can also use an oxyethylene:oxypropylene ratio of about 50:1 or even a ratio of 100:1. Ratios below 1:1 cannot be used because the water solubility of the resultant scouring agent is too small for practical use.

Also provided in accordance with the present invention is a nonionic diester composition which is particularly suitable for use as a low-foam, low-temperature scouring agent when mixed with water having the formula:

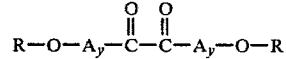

wherein R is alkyl having from 11 to 18 carbon atoms, A is a divalent radical selected from the group consisting of oxyethylene units and random mixtures of oxyethylene units with oxypropylene units up to a ratio of about 1:1; and y is an integer having values of 5 to about 11.

The compositions of the present invention are liquids having a low viscosity which have been found to exhibit a combination of low-foam, good scourability, good wetting, good biogradability, and excellent thermal stability characteristics. Further, they are suitable for use at low temperatures as evidenced by a cloud point of from about 10° C. to about 40° C., affording energy saving capabilities, and the thermal stability thereof makes possible their use in spray dried formulations.

The fatty alcohols used in making the alkylene oxide adducts from which the ester compositions prepared can be primary or secondary having 11 to about 18 carbon atoms. It is preferred to use alcohols containing 11 to about 14 carbon atoms. The alcohols may also be branched although it is preferred to use linear alkyl chains.

The degree of polymerization of the alkylene oxide adducts is about 5 to about 12. Preferably, when ethylene oxide is used in preparing the alkylene oxide adducts the degree of polymerization is from about 7 to about 9, and when random mixtures of alkylene oxides are used, the degree of polymerization is from about 7 to about 11.

The dibasic acid used for making the esters of this invention is, preferably, oxalic acid with malonic being a less desirable dibasic acid. Inferior results are obtained as one goes up in this homologous series as shown in the examples where adipic acid is completely unsatisfactory.

The diester, nonionic scouring agents suitable for use according to the process of the invention may be prepared by methods well known in the art. Various transesterification catalysts can be used, with titanium alkoxides being preferred and tetraisopropyl titanate being most preferred. The esterification reaction is enhanced by using a water-azeotroping agent such as benzene, toluene, and the like.

Esterification temperature is not narrowly critical, but it is preferred to use the temperatures in the range of 100° C. to 180° C., with a temperature range of about 140° to about 170° C. being preferred. Under these conditions, the reaction completed in about 8 to about 12 hours. Pressure is not critical.

The preferred scouring agent embodiments of this invention offer the following improvement over the prior art compositions:
1. improved wetting ability
2. low-foam generation
3. superior scouring ability at 100° F. (37.5° C.)
4. readily bio-oxidized in 20 days
5. liquid having a low viscosity
6. excellent heat stability The concentration of scouring agent is not narrowly critical but it is preferred to use aqueous solutions containing about 0.05 to about 0.2 weight percent of scouring agent therein.

The invention is further described in the examples which follow. All parts and percentages are by weight unless otherwise specified.

EXAMPLE 1

Preparation of Bis(Tergitol 15-S-7) Oxalate

A mixture of 254 grams (0.50 mole) Tergitol 15-S-7 (Trademark of Union Carbide Corporation for an ethylene oxide adduct of a mixture of $C_{11}$–$C_{15}$ isomeric linear alcohols having a molecular weight of 508), 22.4 grams (0.25 mole) of oxalic acid and 1.5 ml of tetraisopropyl titanate was placed in a 4-necked flask fitted with a stirrer, distillation head-reflux condenser, dropping funnel and temperature probe for indirect control of the voltage to the flask's heating mantle. A positive nitrogen pressure was placed on the reactor and the contents of the flask were heated to about 108° C. Approximately 50 ml of benzene was added to the flask and heating was resumed until the benzene-water azeotrope began to reflux. Some benzene was removed at frequent intervals together with a water layer of the azeotrope. This intermittent removal of benzene allowed the kettle temperature to increase slowly from 108° C. to the desired reaction temperature of 160° C. After 7.5 hours the stoichiometric amount of water (9 ml) was removed.

After cooling overnight, the product was decanted from a small layer of solids, stripped at a pressure of 0.5 mm Hg to a kettle temperature of 180° C. and held at 180° C. for fifteen minutes, cooled and filtered using filter aid to remove any salts. The vacuum stripping operation removed benzene and any low-boiling products. Infrared analysis of this amber-colored liquid product suggested formation of an ester. Physical properties and biodegradability were determined on the material and it was evaluated as a potential low-foam surfactant. Pertinent evaluation data are presented in Tables I, II and III.

EXAMPLE 2

Preparation of Bis(Tergitol 15-S-9) Oxalate

A mixture of 150.4 grams (0.25 mole) of Tergitol 15-S-9 (an ethylene oxide adduct of a blend of $C_{11}$ to $C_{15}$ isomeric linear alcohols having an adduct molecular weight of 596 sold by Union Carbide Corporation), 10.8 grams (0.12 mole) of oxalic acid and 0.6 ml of tetraisopropyl titanate was charged to the apparatus described in Example 1. Using the same reaction conditions given in Example 1, a product was obtained after stripping which was a yellow liquid having excellent scouring properties. Evaluation data are presented in Tables I, II and III.

EXAMPLE 3

Preparation of Bis(Tergitol 15-S-12) Oxalate

A mixture of 190.6 grams (0.26 mole) of Tergitol 15-S-12 (trademark for an ethylene oxide adduct of $C_{11}$ to $C_{15}$ isomeric linear alcohols, said adduct having a molecular weight of 728, sold by the Union Carbide Corporation), 10.8 grams (0.12 mole) of oxalic acid and 0.9 ml of tetraisopropyl titanate was charged to the apparatus described in Example 1. Using the same reaction conditions employed in Example 1, a yellow liquid product was obtained having excellent scouring properties after vacuum stripping. Pertinent evaluation data are contained in Tables I, II and III.

The excellent scouring properties of this composition is apparent from the data reported but the cloud point and initial foam is significantly higher than that found for the compositions of Examples 1 and 2 and the biodegradability is significantly less desirable.

TABLE I

| | PERFORMANCE EVALUATION | | | |
| --- | --- | --- | --- | --- |
| | Bis(TERGITOL 15-S-7) Oxalate | Bis(TERGITOL 15-S-9) Oxalate | Bis(TERGITOL 15-S-12) Oxalate | Bis(3 Molar Parts 15-S-9) (1 Molar Part 15-S-7) Oxalate |
| Cloud Point, °C. | 11 | 23.8 | 67.8 | 19 |
| °F. | 52 | 74.8 | 154.0 | 66 |

TABLE I-continued

| | PERFORMANCE EVALUATION | | | |
|---|---|---|---|---|
| | Bis(TERGITOL 15-S-7) Oxalate | Bis(TERGITOL 15-S-9) Oxalate | Bis(TERGITOL 15-S-12) Oxalate | Bis(3 Molar Parts 15-S-9) (1 Molar Part 15-S-7) Oxalate |
| Draves Wetting @ 77° F. (26° C.) | | | | |
| Concentration | | | | |
| 0.05% | — | 40.3 | — | — |
| 0.07% | 45.1 | — | 27.5 | — |
| 0.10% wetting time, seconds | 25.6 | 12.9 | 19.0 | 24.4 |
| 0.15% | 13.5 | 9.35 | — | 12.7 |
| 0.20% | — | 6.65 | 9.9 | 10.2 |
| 20-Sec. Wetting Concentration, % | .116 | .083 | .098 | .11 |
| Ross-Miles Foam @ 122° F. (50° C.) | | | | |
| Initial Foam Height, mm | 25 | 95 | 155 | 30 |
| 5-Min. Foam Height, mm | 20 | 35 | 28 | 25 |
| Waring Blendor Foam @ 77° F. (26° C.) | | | | |
| Initial Foam Vol., ml | 200 | 180 | 330 | 180 |
| Half-Life, Sec. | <1 | 3.5 | 26.7 | <1 |
| Cotton Scouring (Unbuilt) | | | | |
| F. D. Snell Soil Cloth Terg-O-Tometer, 0.1% Concentration 15 Minutes 100 RPM, | | | | |
| % Soil Removal @ 140° F. (60° C.) | 23.3 | 31.4 | 34.0 | 34.8 |
| % Soil Removal @ 100° F. (38° C.) | 16.6 | 34.4 | 28.6 | 32.2 |
| Polyester/Cotton (65/35) Scouring | | | | |
| Testfabrics Soil Cloth, Unfinished Terg-O-Tometer, 0.1% Concentration 0.2% TSPP, 15 Minutes @ 100 RPM | | | | |
| % Soil Removal @ 140° F. | 77.5 | 81.1 | 80.4 | 82.0 |
| % Soil Removal @ 100° F. | 72.6 | 75.9 | 74.8 | 74.0 |
| Surface Tension 77° F. | | | | |
| DuNuoy Tensiometer | | | | |
| 0.1% Concentration, Dynes/cm | 29.2 | 28.4 | 30.3 | 29 |

TABLE II

SUMMARY OF EXPERIMENTAL RESULTS

| | Mol. Wt. | Physical Appearance | Specific Gravity, 25° C. | Viscosity, cps, 25° C. | Cloud Point, °C. | bio-oxidation, % at 20 Days (a) |
|---|---|---|---|---|---|---|
| Bis(TERGITOL 15-S-7) Oxalate | 1070 | Liq. | 1.011 | 96.3 | 11 | 49 |
| Bis(TERGITOL 15-S-9) Oxalate | 1246 | Liq. | 1.014 | 105.0 | 23.8 | 39 |
| Bis(TERGITOL 15-S-12) Oxalate | 1510 | Liq. | 1.036 | 97.2 | 67.8 | 20 |
| Bis(TERGITOL 15-S-9/15-S-7) Oxalate (b) | 1202 | Liq. | 1.013 | 110.2 | 19 | 46 |

(a) Using unacclimated seed.
(b) The TERGITOL nonionics were blended at a 3/1:15-S-9/15-S-7 Mole ratio.

TABLE III

SUMMARY OF EXPERIMENTAL RESULTS THERMAL STABILITY

| | Smoke Point, °C. | Volatility, (a) wt. loss per hr. |
|---|---|---|
| Bis(TERGITOL 15-S-7) Oxalate | 157 | 6.7 |
| Bis(TERGITOL 15-S-9) Oxalate | 152 | 8.1 |
| Bis(TERGITOL 15-S-12) Oxalate | 142 | 3.1 |
| Bis(TERGITOL 15-S-9/15-S-7) Oxalate (b) | 162 | 8.0 |

(a) Volatility tests were carried out at 200° C. using a 10g sample in a pyrex dish having an area of 20 sq. cm.
(b) The TERGITOL nonionics were blended at a 3/1:15-S-9/15-S-7 Mole ratio.

EXAMPLE 4

Preparation of a Mixture of Tergitol 15-S-9 and Tergitol 15-S-7 Oxalates

A mixture of 223.6 grams (0.375 mole) of Tergitol 15-S-9, 63.5 grams (0.125 mole) of Tergitol 15-S-7, 22.5 grams (0.25 mole) of oxalic acid and 1.5 ml of tetraisopropyl titanate was charged to the apparatus described in Example 1. Using the same reaction conditions employed in Example 1, a tan liquid product was obtained after stripping having excellent low-foam characteristics, biodegradability and cotton and polyester/cotton scourability at 100° F. (37.8° C.) and 140° F. (60° C.). Pertinent evaluation data are delineated in Tables I, II and III.

EXAMPLE 5

Preparation of Epal 1214 Ethoxylate Oxalate

Epal 1214 (trademark for a linear primary alcohol mixture having a molecular weight of 200 sold by Ethyl Corporation) was ethoxylated with 7 moles of ethylene oxide per mole Epal 1214. A mixture of 258.0 grams (0.5 mole) of this ethoxylate, 22.5 grams (0.25 mole) of oxalic acid and 1.5 ml of tetraisopropyl titanate was charged to the apparatus described in Example 1. Using the same reaction conditions given in Example 1, a tan liquid product was obtained after vacuum stripping having excellent scouring properties. Evaluation data pertinent to this product are presented in Tables IV, V and VI.

EXAMPLE 6

Preparation of Epal 1214 Alkoxylate Oxalate

Epal 1214 was alkoxylated in a random manner with a mixture of 7.5 mole of ethylene oxide and 0.6 mole propylene oxide per mole of Epal 1214 using an alkaline catalyst. A mixture of 286.0 grams (0.5 mole) of Epal 1214 alkoxylate, 22.5 grams oxalic acid (0.25 mole) and 1.5 ml of tetraisopropyl titanate was charged to the apparatus described in Example 1. Using the same reaction conditions employed in Example 1, an amber liquid product having excellent low-foaming and scouring properties was obtained after vacuum stripping. Pertinent evaluation data are contained in Tables IV, V and VI.

EXAMPLE 7

Preparation of Epal 1214 Alkoxylate Oxalate

A random alkoxylate of Epal 1214 was prepared using 8 moles of ethylene oxide and 1.5 moles of propylene oxide per mole of Epal 1214 with an alkaline catalyst. A mixture of 253.6 grams (0.4 mole) of this Epal 1214 alkoxylate, 18.0 grams (0.2 mole) of oxalic acid and 1.4 ml tetraisopropyl titanate was charged to the apparatus described in Example 1. Using the same reaction conditions given in Example 1, an amber colored liquid product was obtained after vacuum stripping having excellent low-foaming characteristics, biodegradability, cotton and polyester/cotton scourability at 100° F. and 140° F. Pertinent evaluation data are presented in Tables IV, V and VI.

EXAMPLE 8

Preparation of Epal 1214 Alkoxylate Oxalate

A random alkoxylate of Epal 1214 was prepared with 8 moles of ethylene oxide and 3 moles of propylene oxide per mole of Epal 1214 using an alkaline catalyst. A mixture of 264.0 grams (0.35 mole) of this Epal alkoxylate, 15.7 grams (0.175 mole) of oxalic acid, and 1.5 ml of tetraisopropyl titanate was charged to the apparatus described in Example 1. Using the same conditions and procedures employed in Example 1, a tan-colored liquid product was obtained after stripping having excellent low-foaming characteristics, biodegradability, and polyester/cotton scourability at 100° F. and 140° F.

EXAMPLE 9

Preparation of Epal 1214 Alkoxylate Oxalate

Epal 1214 was alkoxylated with blocks of 0.7 moles propylene oxide and 8 moles of ethylene oxide per mole of Epal 1214 using an alkaline catalyst. A mixture of 240.8 grams (0.4 mole) of this alkoxylated Epal 1214, 18.0 grams (0.2 mole) of oxalic acid and 1.3 ml of tetraisopropyl titanate was charged to the apparatus described in Example 1. Using the same reaction conditions as described in Example 1, an amber liquid product was obtained after vacuum stripping having excellent scouring properties. Pertinent evaluation data are presented in Tables IV, V and VI.

EXAMPLE 10

Preparation of Tergitol NPX Oxalate

A mixture of 272.8 grams (0.4 mole) of Tergitol NPX (tradename of Union Carbide Corporation for ethoxylated nonylphenol containing 10.5 moles of ethylene oxide), 18.0 grams (0.2 mole) of oxalic acid and 1.5 ml of tetraisopropyl titanate was charged to the apparatus described in Example 1. Following the procedure and conditions described in Example 1, an amber liquid having excellent scouring properties was obtained after vacuum stripping. Evaluation data are presented in Tables IV, V and VI.

TABLE IV

| | Bis(EPAL 1214 . 7EO) Oxalate | Bis(EPAL 1214 . 7.5EO/ 0.6PO)(a) Oxalate | Bis(EPAL 1214 . 8EO/ 1.5PO) Oxalate | Bis(EPAL 1214 . 8EO/ 3PO) Oxalate | Bis(EPAL 1214 . 0.7PO/ 8EO) Oxalate(b) | Bis(NPX) Oxalate |
|---|---|---|---|---|---|---|
| PERFORMANCE EVALUATION | | | | | | |
| Cloud Point, °C. | 23.6 | 28.3 | 40.0 | 37.6 | 42.0 | 26.0 |
| °F. | 74.5 | 83.0 | 104.0 | 99.7 | 107.6 | 78.8 |
| Draves Wetting @ 77° F. (26° C.) | | | | | | |
| Concentration | | | | | | |
| 0.05% | — | — | 57.0 | 31.6 | 55.0 | 42.0 |
| 0.10% | — | — | 25.9 | 17.5 | 29.0 | 23.0 |
| 0.20% wetting time, seconds | 20.7 | 16.0 | 10.8 | 8.2 | 16.4 | 12.8 |
| 0.30% | 18.4 | 12.2 | 7.2 | — | 10.7 | 8.8 |
| 0.40% | 15.7 | 9.0 | — | — | — | — |
| 20-Sec. Wetting Concentration, % | .23 | .148 | .122 | .083 | .155 | .166 |
| Ross-Miles Foam @ 122° F. (50° C.) | | | | | | |
| Initial Foam Height, mm | 80 | 35 | 45 | 15 | 95 | 100 |
| 5-Min. Foam Height, mm | 65 | 30 | 18 | 5 | 85 | 90 |
| Waring Blendor Foam @ 77° F. (26° C.) | | | | | | |
| Initial Foam Vol, ml | 190 | 210 | 270 | 270 | 270 | 220 |
| Half-Life, Sec. | 5 | 7 | 12 | 17 | 13 | 10 |
| Cotton Scouring (Unbuilt) | | | | | | |
| F. D. Snell Soil Cloth | | | | | | |
| Terg-O-Tometer, 0.1% Concentration | | | | | | |
| 15 Minutes @ 100 RPM, | | | | | | |
| % Soil Removal @ 140° F. (60° C.) | 26.4 | 24.1 | 35.4 | 13.3 | 36.1 | 37.5 |
| % Soil Removal @ 100° F. (38° C.) | 23.8 | 24.1 | 29.3 | 26.7 | 26.9 | 33.2 |
| Polyester/Cotton (65/35) Scouring | | | | | | |
| Testfabrics Soil Cloth | | | | | | |
| Terg-O-Tometer, 0.1% Concentration | | | | | | |
| 0.2% TSPP, 15 Minutes @ 100 RPM | | | | | | |
| % Soil Removal @ 140° F. (60° C.) | 86.1 | 86.2 | 88.1 | 90.5 | 89.1 | 88.4 |

TABLE IV-continued

| | PERFORMANCE EVALUATION | | | | | |
|---|---|---|---|---|---|---|
| | Bis(EPAL 1214 . 7EO) Oxalate | Bis(EPAL 1214 . 7.5EO/ 0.6PO)[a] Oxalate | Bis(EPAL 1214 . 8EO/ 1.5PO) Oxalate | Bis(EPAL 1214 . 8EO/ 3PO) Oxalate | Bis(EPAL 1214 . 0.7PO/ 8EO) Oxalate[b] | Bis(NPX) Oxalate |
| % Soil Removal @ 100° F. (38° C.) | 81.1 | 80.2 | 83.1 | 84.2 | 82.1 | 83.0 |

[a]EO = Ethylene oxide and PO = Propylene oxide
[b]In this ester the oxide polymer system was block in place of random with the propylene oxide added first to the fatty alcohol.

TABLE V

| | SUMMARY OF EXPERIMENTAL RESULTS | | | | | |
|---|---|---|---|---|---|---|
| | Mol. Wt. | Physical Appearance | Specific Gravity, 25° C. | Viscosity, cps, 25° C. | Cloud Point, °C. | Bio-oxidation, % at 20 Days[a] |
| Bis(EPAL 1214 . 7EO) Oxalate[b] | 1086 | Liq. | 1.006 | 92.1 | 23.6 | 46 |
| Bis(EPAL 1214 . 7.5EO/0.6PO) Oxalate | 1198 | Liq. | 1.006 | 91.9 | 28.3 | 68 |
| Bis(EPAL 1214 . 8EO/1.5PO) Oxalate | 1322 | Liq. | 1.007 | 74.0 | 40.0 | 47 |
| Bis(EPAL 1214 . 8EO/3PO) | 1510 | Liq. | 0.999 | 100.9 | 37.6 | 45 |
| Bis(EPAL 1214 . 0.7PO/8EO) Oxalate[c] | 1258 | Liq. | 1.008 | 79.3 | 42.0 | 53 |
| Bis(NXP) Oxalate[d] | 1418 | Liq. | 1.073 | 388.1 | 26.0 | 41,37[e] |

[a]Using unacclimated seed.
[b]EPAL 1214 is a linear primary alcohol mixture, average molecular weight-200, sold by the Ethyl Corp; the moles of alkylene oxide are approx. numbers.
[c]In this ester the oxide polymer system was block in place of random with the propylene oxide added first to the fatty alcohol.
[d]TERGITOL NPX is the UCC trade name for nonylphenol plus 10.5 moles of ethylene oxide.
[e]The bio-oxidation of bis Tergitol (NPX) oxalate is unpredictably high; the seed bacteria was very active considering that the precursor Tergitol NPX also showed in 20 days 35 percent bio-oxidation.

TABLE VI

| | SUMMARY OF EXPERIMENTAL RESULTS THERMAL STABILITY | |
|---|---|---|
| | Smoke Point, °C. | Volatility,[a] wt. loss per hr. |
| Bis(EPAL 1214 . 7EO) Oxalate[b] | 149 | 7.8 |
| Bis(EPAL 1214 . 7.5EO/0.60PO) Oxalate | 158 | 7.8 |
| Bis(EPAL 1214 . 8EO/1.5PO) Oxalate | 160 | 8.2 |
| Bis(EPAL 1214 . 8EO/3PO) Oxalate | 166 | 7.9 |
| Bis(EPAL 1214 . 7PO/8EO) Oxalate[c] | 155 | 9.1 |
| Bis Tergitol (NPX) Oxalate[d] | 202 | 1.2 |

[a]Volatility tests were carried out at 200° C. using a 10g sample in a pyrex dish having an area of 20 sq. cm.
[b]EPAL 1214 is a linear primary alcohol mixture, average molecular weight-200, sold by the Ethyl Corp; the moles of alkylene oxide are approximate numbers.
[c]In this ester the oxide polymer system was block in place of random with the propylene oxide added first to the fatty alcohol.
[d]TERGITOL NPX is the UCC trade name for nonylphenol plus 10.5 moles of ethylene oxide.

CONTROL A

Preparation of Bis(Tergitol 15-S-9)Adipate

A mixture of 238.0 grams (0.4 mole) of Tergitol 15-S-9, 29.0 grams (0.2 mole) of adipic acid and 1.0 ml of tetraisopropyl titanate was charged to the apparatus described in Example 1. Using the same procedures and reaction conditions employed in Example 1, an amber liquid product was obtained after vacuum stripping. Evaluation of the product having a cloud point below 32° F. (0° C.) and a cotton scourability at 140° F. (60° C.) of 0%, indicates that this adipate ester is a poor scouring agent.

Performance Evaluation Tests

Performance evaluation of the scouring agents disclosed herein was effected by means of the following tests:

DRAVES WETTING (was measured in accordance with AATCC Method No. 17-1952.

ROSS-MILES FOAM (was determined in accordance with ASTM D 1173-53.

WARING BLENDER Foam Test is described below:

Dissolve 0.5 ml of the sample (0.5 g. if solid) in 99.5 ml. of distilled water. Transfer solution to the glass mixing jar, graduated to show the measure of volume, of the Waring Blender. Place the jar on the base of the mixer, cover the jar, and turn the stirrer on. After mixing for 30 seconds, turn the stirrer off. Read the initial foam volume and record. This volume is determined by reading the top of the main body of foam, disregarding any large bubbles that may appear above the compact foam. Half-life is the time required for 50 ml of solution (one half of the original volume) to layer out of the foam. Determine half-life by subtracting the 30-second mixing time from the total time required to reach the 50 ml point. When the test is used at elevated temperatures, the test solution is preheated to the desired temperature and then added to the mixing jar. Some temperature-drop will necessarily occur during the test, because no provision is made to hold the temperature constant.

COTTON SCOURING (Unbuilt) was determined as shown below:

Four 4-inch by 4-inch swatches of F. D. Snell standard soil cloth were placed in beakers containing 1000 ml of scouring solution which contained surfactant only (unbuilt), in tap water containing about 50 ppm of hardness. The scouring beakers were placed in the Terg-O-Tometer bath and heated therein to the desired scouring temperature. The scouring solutions were then agitated for 15 minutes at 100 rpm. The swatches were removed from the solution and thoroughly rinsed in a stream of running warm tap water. After passage through nip rolls, they were further dried by ironing. The reflectance of each was measured using a Photovolt Reflectometer, Model 670, standardized with a white porcelain plate, and using a tristimulus filter. Soil removal was calculated using the Harris equation, as follows:

$$\% \text{ Soil Removal} = \frac{A - B}{C - B} \times 100$$

where

A = reflectance of soiled swatches after scouring
B = reflectance of soiled swatches before scouring
C = reflectance of unsoiled swatch.

POLYESTER/COTTON (65/35) Scouring is described as follows:

Four 4-inch by 4-inch swatches of Testfabrics standard soiled 65/35 polyester/cotton white shirting without finish were scoured in the Terg-O-Tometer in aqueous solutions containing 0.1 percent of surfactant and 0.2 percent of tetrasodiumpyrophosphate (TSPP). Other test conditions and equipment were as previously described under Cotton Scouring. Soil Removal was calculated using the Kubelka-Munke equation, as follows:

$$\% \text{ Soil Removal} = \frac{K/S \text{ Soiled} - K/S \text{ Scoured}}{K/S \text{ Soiled} - K/S \text{ Unsoiled}} \times 100$$

$$\text{where } \frac{K}{S} = \frac{(1-R)^2}{2R}, R = \text{Reflectance}$$

SURFACE TENSION was measured in accordance with ASTM D 1331-56 at 77° F. (26° C.).

BIO-OXIDATION determinations were made by the procedure described in "Standard Methods for the Examination of Water and Wastewater," APHA, pg. 543.

$$\% \text{ Bio-oxidation} = \frac{\text{BOD}}{\text{THOD}} \text{ (Biochemical Oxidation Demand)}$$

where THOD is based on the theoretical oxidation of the test material to its lowest energy state (i.e. $CO_2$, $H_2O$), except for nitrogen containing products. The THOD of nitrogen containing materials is based on the nitrogen reaching and remaining in the ammonia form. Although this is not the ultimate end product in nature, the static BOD test system usually inhibits the nitrifying bacteria so that very little if any nitrogenous oxygen demand is measured. The chemical oxygen demand analytical procedure is used to actually oxidize the test material in a chromic acid reflux system. This value is reported as the measured carbonaceous THOD.

SMOKE POINT was determined as described below:

30 cc of fluid are placed into a glass 50 cc beaker and the beaker and contents are placed on a Mag-mix hot plate. A stirring bar and thermometer are inserted into the fluid and the fluid is mixed with moderate agitation. The temperature of the hot plate is controlled at 260° C. The temperature is recorded (smoke point) when the first sign of visible smoke appears.

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. A low temperature, low-foam, biodegradable scouring agent having the formula:

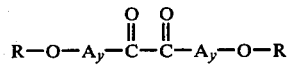

wherein R is a monovalent alkyl radical having about 11 to about 18 carbon atoms, A is a divalent radical selected from the group consisting of oxyethylene units and random mixtures of oxyethylene units with up to 1 part of oxypropylene units per unit of oxyethylene and y is an integer having values of 5 to about 11.

2. Scouring agent claimed in claim 1 wherein A is an oxyethylene group.

3. Scouring agent claimed in claim 2 wherein y is an integer in the range of about 7 to about 9.

4. Scouring agent claimed in claim 1 wherein the ratio of oxyethylene to oxypropylene units is in the range of about 1:1 to about 50:1.

5. Scouring agent claimed in claim 4 wherein y is an integer in the range of about 7 to about 11.

6. Scouring agent claimed in claim 1 wherein said scouring agent has a cloud point in the range from about 10° C. to about 40° C.

7. Method of cleaning cotton or polyester-cotton articles under conditions of low temperature and low foam which comprises contacting said cotton or polyester/cotton articles with an aqueous solution of a nonionic detergent having the formula:

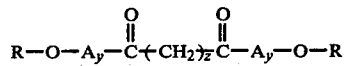

wherein R is a monovalent radical selected from the group consisting of alkyl having 11 to about 18 carbon atoms and alkyl-substituted phenyl wherein the alkyl contains about 7 to 12 carbon atoms, A is a divalent radical selected from the group consisting of oxyethylene units and mixture of oxyethylene units containing up to 1 part of oxypropylene units per unit of oxyethylene, y is an integer having values of about 5 to about 12, and z is an integer having values of 0 to 1.

8. The method of claim 7 in which R is a monovalent alkyl radical and y is an integer having values in the range of about 7 to about 11.

9. The method of claim 8 in which said nonionic detergent has a cloud point in the range from about 10° C. to about 40° C.

10. The method of claim 8 in which A is a random mixture of oxyethylene and oxypropylene units.

* * * * *